United States Patent
Yamada

(10) Patent No.: US 8,933,964 B2
(45) Date of Patent: Jan. 13, 2015

(54) IMAGE DISPLAY METHOD AND APPARATUS

(75) Inventor: Hideyuki Yamada, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 203 days.

(21) Appl. No.: 13/566,247

(22) Filed: Aug. 3, 2012

(65) Prior Publication Data

US 2013/0044126 A1 Feb. 21, 2013

(30) Foreign Application Priority Data

Aug. 16, 2011 (JP) ................ 2011/177843

(51) Int. Cl.
| | | |
|---|---|---|
| G09G 5/00 | (2006.01) | |
| G06T 5/50 | (2006.01) | |
| H04N 7/18 | (2006.01) | |
| A61B 1/04 | (2006.01) | |
| G02B 23/24 | (2006.01) | |
| G02B 27/10 | (2006.01) | |

(52) U.S. Cl.
CPC *G06T 5/50* (2013.01); *H04N 7/183* (2013.01); *A61B 1/043* (2013.01); *G02B 23/2453* (2013.01); *G02B 27/1013* (2013.01); *G06T 2207/10064* (2013.01); *G06T 2207/10068* (2013.01); *G06T 2207/20221* (2013.01)
USPC .......................................... 345/629; 345/619

(58) Field of Classification Search
USPC ................................................ 600/178, 476
See application file for complete search history.

(56) References Cited

U.S. PATENT DOCUMENTS

| | | | | |
|---|---|---|---|---|
| 6,582,363 | B2 * | 6/2003 | Adachi et al. ............... | 600/178 |
| 7,892,169 | B2 * | 2/2011 | Gono et al. .................. | 600/178 |
| 2002/0026099 | A1 * | 2/2002 | Adachi et al. ............... | 600/178 |
| 2007/0073104 | A1 | 3/2007 | Iketani et al. | |
| 2007/0203413 | A1 * | 8/2007 | Frangioni ..................... | 600/478 |
| 2010/0262017 | A1 * | 10/2010 | Frangioni ..................... | 600/476 |
| 2010/0305455 | A1 * | 12/2010 | Frangioni ..................... | 600/476 |
| 2011/0152692 | A1 * | 6/2011 | Nie et al. ..................... | 600/473 |
| 2011/0237895 | A1 * | 9/2011 | Yoshida et al. .............. | 600/180 |
| 2011/0295062 | A1 * | 12/2011 | Gratacos Solsona et al. | 600/109 |
| 2011/0319712 | A1 * | 12/2011 | Kuroda et al. ............... | 600/109 |
| 2012/0116159 | A1 * | 5/2012 | Mizuyoshi et al. .......... | 600/109 |

FOREIGN PATENT DOCUMENTS

| | | | |
|---|---|---|---|
| JP | 9-154812 | A | 6/1997 |
| JP | 2002-010968 | A | 1/2002 |
| JP | 2005-349007 | A | 12/2005 |
| JP | 2006-175052 | A | 7/2006 |
| JP | 2008-259591 | A | 10/2008 |

* cited by examiner

*Primary Examiner* — M Good Johnson
(74) *Attorney, Agent, or Firm* — McGinn IP Law Firm, PLLC

(57) ABSTRACT

A visible image based on light output from a region to be observed by illumination of the region to be observed with visible light, and a special image based on light output from the region to be observed by illumination of the region to be observed with special light in a wavelength band that is different from the wavelength band of the visible light are obtained. An extraction image is generated by extracting a part of image data representing the visible image. A superimposition image is generated by superimposing the generated extraction image on the special image. The generated superimposition image is displayed.

14 Claims, 5 Drawing Sheets

FIG.6
ORDINARY IMAGE
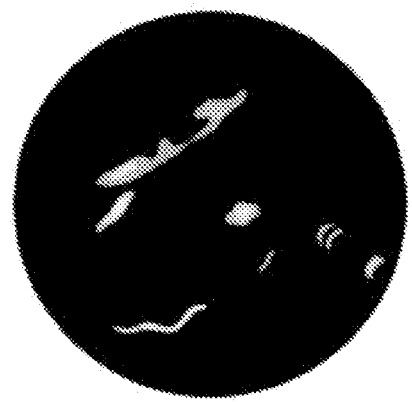
FLUORESCENCE IMAGE
FIG.7
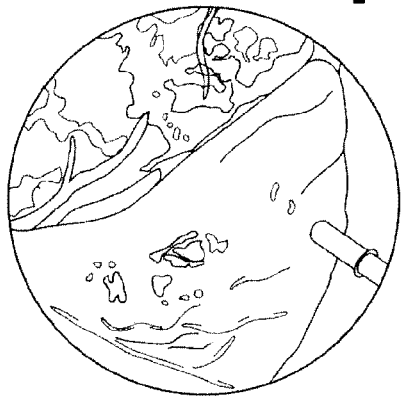
ORDINARY IMAGE
SUPERIMPOSITION IMAGE

IMAGE DISPLAY METHOD AND APPARATUS

BACKGROUND OF THE INVENTION

1. Field of the Invention

The present invention relates to an image display method and apparatus for displaying a special image of a region to be observed obtained by illumination of the region to be observed with special light.

2. Description of the Related Art

Conventionally, endoscope systems for observing tissues in patients' body cavities were widely known. Further, electronic endoscope systems that obtain ordinary images of regions to be observed in patients' body cavities by illuminating the regions with white light, and that display the ordinary images on monitor screens were widely used in practical applications.

As such endoscope systems, for example, a fluorescence endoscope system that obtains an autofluorescence image as well as an ordinary image, and that displays the two images on a monitor screen has been proposed. The fluorescence endoscope system obtains the autofluorescence image by imaging an image of autofluorescence output from the region to be observed by illumination with excitation light.

As the fluorescence endoscope system, a system obtaining a fluorescence image, for example, by injecting ICG (indocyanine green) into a patient's body in advance, and by detecting fluorescence of ICG in patient's blood vessels by illumination of a region to be observed with excitation light has been proposed.

Here, fluorescence images obtained in the aforementioned endoscope systems do not represent an entire region to be observed, such as an organ, but only a light output portion of the region to be observed. Therefore, when the fluorescence image is observed alone, the light output portion of the region to be observed may be observed, but a surrounding region of the light output portion is not observable. Hence, it is impossible to recognize where the light output portion is located in the region to be observed.

To solve such a problem, for example, an ordinary image and a fluorescence image may be displayed at the same time. However, since the two images are displayed separately, it is still impossible to accurately recognize where the light output portion of the fluorescence image is located in the ordinary image.

Therefore, for example, Japanese Unexamined Patent Publication No. 9(1997)-154812 (Patent Document 1), Japanese Unexamined Patent Publication No. 2002-010968 (Patent Document 2), Japanese Unexamined Patent Publication No. 2005-349007 (Patent Document 3), Japanese Unexamined Patent Publication No. 2006-175052 (Patent Document 4), and U.S. Patent Application Publication No. 20070073104 (Patent Document 5) propose recognizing the location of a light output portion of a fluorescence image by generating new synthesis image signals by combining ordinary image signals representing an ordinary image and fluorescence image signals representing a fluorescence image together, and by displaying a synthesis image based on the synthesis image signals.

Further, Japanese Unexamined Patent Publication No. 2008-259591 (Patent Document 6) proposes another method for recognizing the location of a light output portion of a fluorescence image. In Patent Document 6, a light output portion of the fluorescence image and a background image of the light output portion are observed by illuminating a region to be observed with excitation light and by illuminating the region to be observed with illumination light including the wavelength band of fluorescence.

However, when a synthesis image is generated by combining an ordinary image and a fluorescence image together, as in Patent Documents 1 through 5, there is a risk that necessary information becomes unobtainable because it becomes difficult to observe the gradation or the like of the light output portion of the fluorescence image.

Further, when a region to be observed is illuminated with illumination light including the wavelength band of fluorescence, as in Patent Document 6, it is necessary to additionally provide an optical filter, a light source, and the like. Hence, a cost for production increases, and the size of the apparatus becomes large.

SUMMARY OF THE INVENTION

In view of the foregoing circumstances, it is an object of the present invention to provide an image display method and apparatus that display an image that makes it possible to accurately recognize the location of a light output portion of a fluorescence image in a region to be observed, and that accurately represents information, such as the gradation of the light output portion.

An image display apparatus of the present invention is an image display apparatus comprising:

an image obtainment unit that obtains a visible image based on light output from a region to be observed by illumination of the region to be observed with visible light, and a special image based on light output from the region to be observed by illumination of the region to be observed with special light in a wavelength band that is different from the wavelength band of the visible light;

an extraction image generation unit that generates an extraction image by extracting a part of image data representing the visible image;

a superimposition processing unit that generates a superimposition image by superimposing the extraction image generated by the extraction image generation unit on the special image; and a display unit that displays the superimposition image generated by the superimposition processing unit.

In the image display apparatus of the present invention, the extraction image generation unit may generate the extraction image by extracting at least one outline included in the visible image.

Alternatively, the extraction image generation unit may generate the extraction image by extracting at least one closed region having a predetermined size or larger included in the visible image.

Further, the display unit may display in such a manner that it does not display the superimposition image, but displays the special image on which the extraction image is not superimposed when the size of a portion of the special image that represents a region outputting light by illumination with the special light is greater than or equal to a predetermined threshold value.

Further, the apparatus may further include an outline enhancement processing unit that performs outline enhancement processing on the visible image, and the display unit may display the visible image on which the outline enhancement processing has been performed.

The special light may be excitation light.

The excitation light may be near infrared light.

The visible light may be white light.

An image display method of the present invention is an image display method comprising the steps of:

obtaining a visible image based on light output from a region to be observed by illumination of the region to be observed with visible light, and a special image based on light output from the region to be observed by illumination of the region to be observed with special light in a wavelength band that is different from the wavelength band of the visible light;

generating an extraction image by extracting a part of image data representing the visible image;

generating a superimposition image by superimposing the generated extraction image on the special image; and displaying the generated superimposition image.

According to the image display method and apparatus of the present invention, a visible image is obtained by illumination of a region to be observed with visible light, and a special image is obtained by illumination of the region to be observed with special light in a wavelength band that is different from the wavelength band of the visible light. Further, an extraction image is generated by extracting a part of image data representing the visible image. Further, a superimposition image is generated by superimposing the generated extraction image on the special image, and the generated superimposition image is displayed. Therefore, it is possible to accurately recognize where the light output portion of the special image is located in the visible image by observing the superimposition image. Further, it is possible to display an image that accurately represents information, such as the gradation of the light output portion.

BRIEF DESCRIPTION OF THE DRAWINGS

FIG. 6 is a diagram illustrating an example of an ordinary image and a fluorescence image; and FIG. 7 is a diagram illustrating an example of an ordinary image and a superimposition image.

DESCRIPTION OF THE PREFERRED EMBODIMENTS

Figure 1:
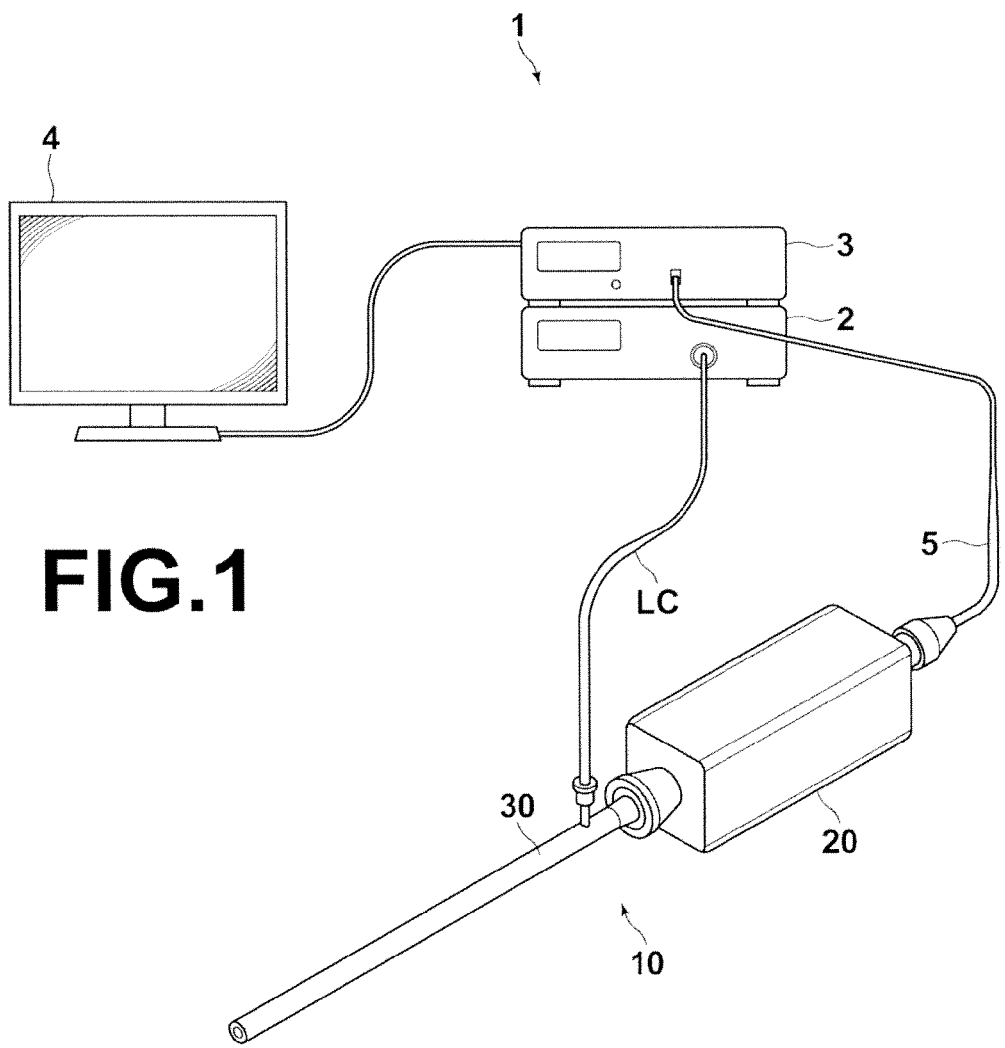
FIG. 1 is a schematic diagram illustrating the structure of a rigid endoscope system using an embodiment of an image display apparatus of the present invention.

Hereinafter, a rigid endoscope system using an image display apparatus according to an embodiment of the present invention will be described in detail with reference to drawings. FIG. 1 is a schematic external view illustrating the structure of a rigid endoscope system 1 according to an embodiment of the present invention.

As illustrated in FIG. 1, the rigid endoscope system 1 of the present embodiment includes alight source apparatus 2, a rigid endoscope imaging apparatus 10, a processor 3, and a monitor 4 (corresponding to a display unit). The light source apparatus 2 outputs ordinary light of white light and excitation light. The rigid endoscope imaging apparatus 10 guides ordinary light and excitation light output from the light source apparatus 2, and illuminates a region to be observed with the ordinary light and the excitation light. Further, the rigid endoscope imaging apparatus 10 images an ordinary image based on reflection light that has been reflected from the region to be observed by illumination with the ordinary light and a fluorescence image based on fluorescence that has been output from the region to be observed by illumination with the excitation light. The processor 3 performs predetermined processing on image signals obtained by imaging by the rigid endoscope imaging apparatus 10. The monitor 4 displays, based on display control signals generated by the processor 3, an ordinary image, a fluorescence image, and a superimposition image, which will be described later, of the region to be observed.

As illustrated in FIG. 1, the rigid endoscope imaging apparatus 10 includes a body cavity insertion unit 30, and an imaging unit 20. The body cavity insertion unit 30 is inserted into a patient's body cavity. The imaging unit 20 images an ordinary image and a fluorescence image of the region to be observed, which have been guided by the body cavity insertion unit 30.

Figure 2:
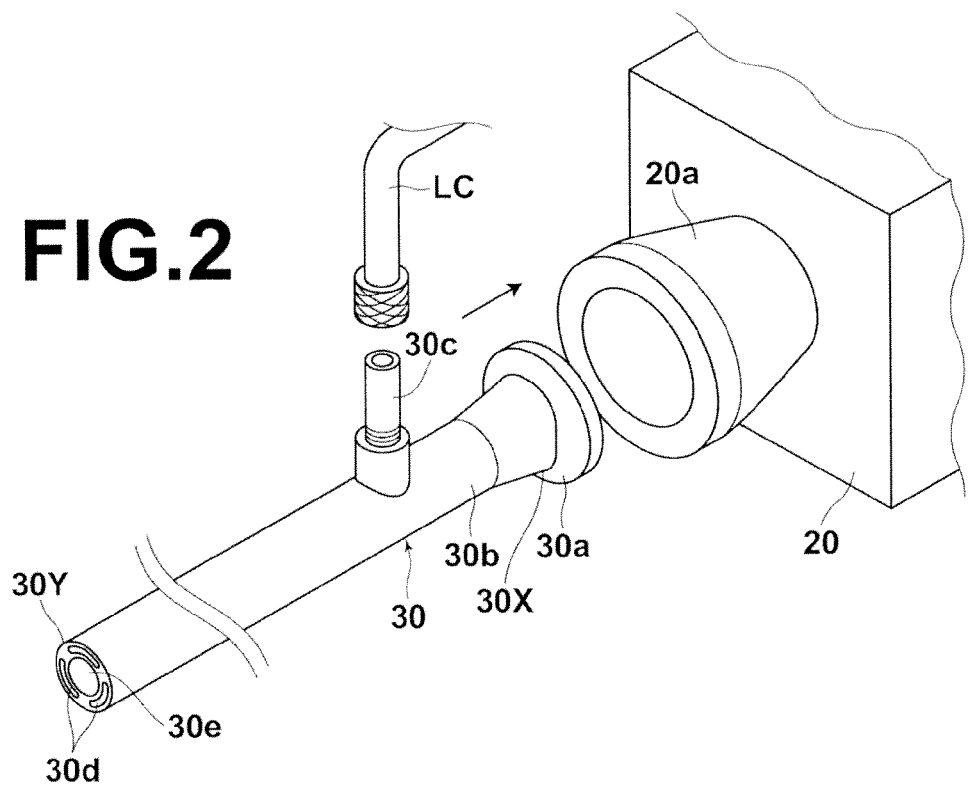
FIG. 2 is a schematic diagram illustrating the structure of a body cavity insertion unit.

As illustrated in FIG. 2, in the rigid endoscope imaging apparatus 10, the body cavity insertion unit 30 and the imaging unit 20 are attachably and detachably connected to each other. The body cavity insertion unit 30 includes a connection member 30a, an insertion member 30b, a cable connection opening 30c, an illumination window or windows 30d, and an imaging window 30e.

The connection member 30a is provided at end 30X of the body cavity insertion unit 30 (insertion member 30b). The imaging unit 20 and the body cavity insertion unit 30 are attachably and detachably connected to each other, for example, by fitting the connection member 30a into an opening 20a formed on the imaging unit 20 side.

The insertion member 30b is inserted into a body cavity when the inside of the body cavity is imaged. The insertion member 30b is made of rigid material, and has a cylindrical shape with a diameter of approximately 5 mm for example. A lens group for forming an image of a region to be observed is housed in the inside of the insertion member 30b. An ordinary image and a fluorescence image of the region to be observed enter the insertion member 30b through the imaging window 30e located at other end 30Y, and are output to the imaging unit 20 side located on the end 30X side through the lens group.

The cable connection opening 30c is provided on a side of the insertion member 30b, and an optical cable LC is mechanically connected to the cable connection opening 30c. Accordingly, the light source apparatus 2 and the insertion member 30b are optically connected to each other through the optical cable LC. The optical cable LC is composed of a so-called bundle fiber (a bundle of fibers) that guides ordinary light and excitation light.

The illumination window or windows 30d are provided at the other end 30Y side of the body cavity insertion unit 30. The illumination window or windows 30d are provided to illuminate the region to be observed with the ordinary light and the excitation light that have been guided by the optical cable LC. Further, a bundle fiber (not illustrated) for guiding the ordinary light and the excitation light from the cable connection opening 30c to the illumination window or windows 30d is housed in the insertion member 30b. The illumination window or windows 30d are formed by polishing a leading end of the bundle fiber.

Figure 3:
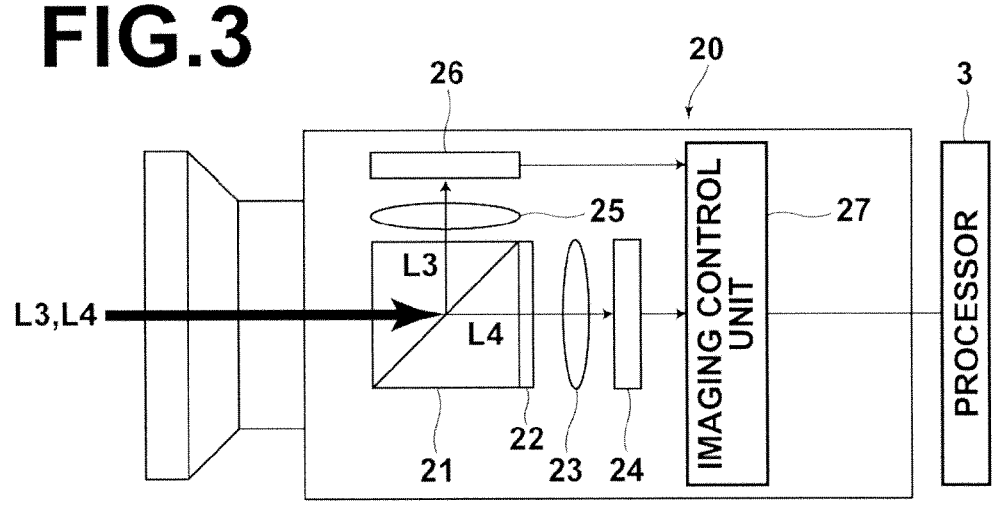
FIG. 3 is a schematic diagram illustrating the structure of an imaging unit.

FIG. 3 is a schematic diagram illustrating the structure of the imaging unit 20. The imaging unit 20 includes a first imaging system and a second imaging system. The first imaging system generates fluorescence image signals of a region to be observed by imaging a fluorescence image of the region to be observed formed by the lens group in the body cavity insertion unit 30. The second imaging system generates ordinary image signals of the region to be observed by imaging an ordinary image of the region to be observed formed by the lens group in the body cavity insertion unit 30. These imaging systems are divided into two optical axes orthogonal to each other by a dichroic prism 21 having spectral characteristics of reflecting an ordinary image and passing a fluorescence image.

The first imaging system includes an excitation light cut filter 22, a first image formation optical system 23, and a high sensitivity imaging device 24. The excitation light cut filter 22 cuts light that has been reflected by the region to be observed and has passed through the dichroic prism 21, and the wavelength of which is less than or equal to the wavelength of excitation light. The excitation light cut filter 22 passes illumination light in a wavelength range of fluorescence, which will be described later. The first image formation optical system 23 forms an image of fluorescence image L4 that has been output from the body cavity insertion unit 30 and has passed through the dichroic prism 21 and the excitation light cut filter 22. The high sensitivity imaging device 24 images the fluorescence image L4 formed by the first image formation optical system 23.

The second imaging system includes a second image formation optical system 25 and an imaging device 26. The second image formation optical system 25 forms an image of ordinary image L3 that has been output from the body cavity insertion unit 30 and reflected by the dichroic prism 21. The imaging device 26 images the ordinary image L3 formed by the second image formation optical system 25.

The high sensitivity imaging device 24 detects light in the wavelength band of fluorescence image L4 at high sensitivity, and converts the light into fluorescence image signals, and outputs the fluorescence image signals. In the present embodiment, an imaging device that images monochromatic images is used as the high sensitivity imaging device 24.

The imaging device 26 detects light in the wavelength band of an ordinary image, and converts the light into ordinary image signals, and outputs the ordinary image signals. A three primary color filter of red (R), green (G) and blue (B) or a CMY color filter of cyan (C), magenta (M) and yellow (Y) in a Bayer arrangement or a honeycomb arrangement is provided on the imaging plane of the imaging device 26.

Further, an imaging control unit 27 is provided in the imaging unit 20. The imaging control unit 27 performs CDS/AGC (correlated double sampling/automatic gain control) processing and A/D conversion processing on the fluorescence image signals that have been output from the high sensitivity imaging device 24 and the ordinary image signals that have been output from the imaging device 26, and outputs the processed signals to the processor 3 through a cable 5 (please refer to FIG. 1).

Figure 4:
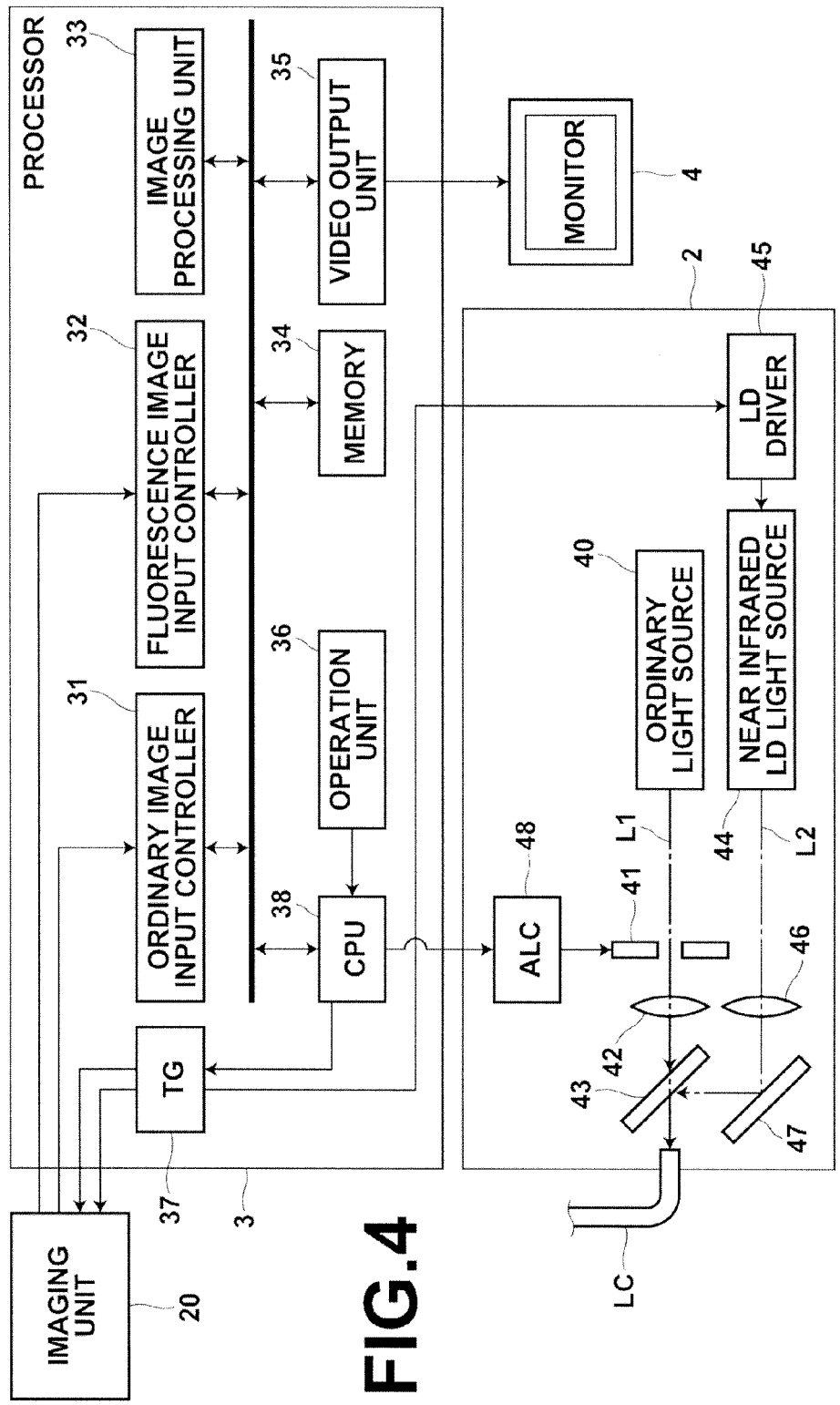
FIG. 4 is a schematic block diagram illustrating the configuration of an image processing apparatus and a light source apparatus.

As illustrated in FIG. 4, the processor 3 includes an ordinary image input controller 31, a fluorescence image input controller 32, an image processing unit 33, a memory 34, a video output unit 35, an operation unit 36, a TG (timing generator) 37, and a CPU 38.

Each of the ordinary image input controller 31 and the fluorescence image input controller 32 includes a line buffer of a predetermined capacity. The ordinary image input controller 31 temporarily stores, for each frame, the ordinary image signals that have been output from the imaging control unit 27 of the imaging unit 20. The fluorescence image input controller 32 temporarily stores the fluorescence image signals. The ordinary image signals stored in the ordinary image input controller 31 and the fluorescence image signals stored in the fluorescence image input controller 32 are stored in the memory 34 through a bus. In the present embodiment, the ordinary image input controller 31 and the fluorescence image input controller 32 correspond to an image obtainment unit.

Figure 5:
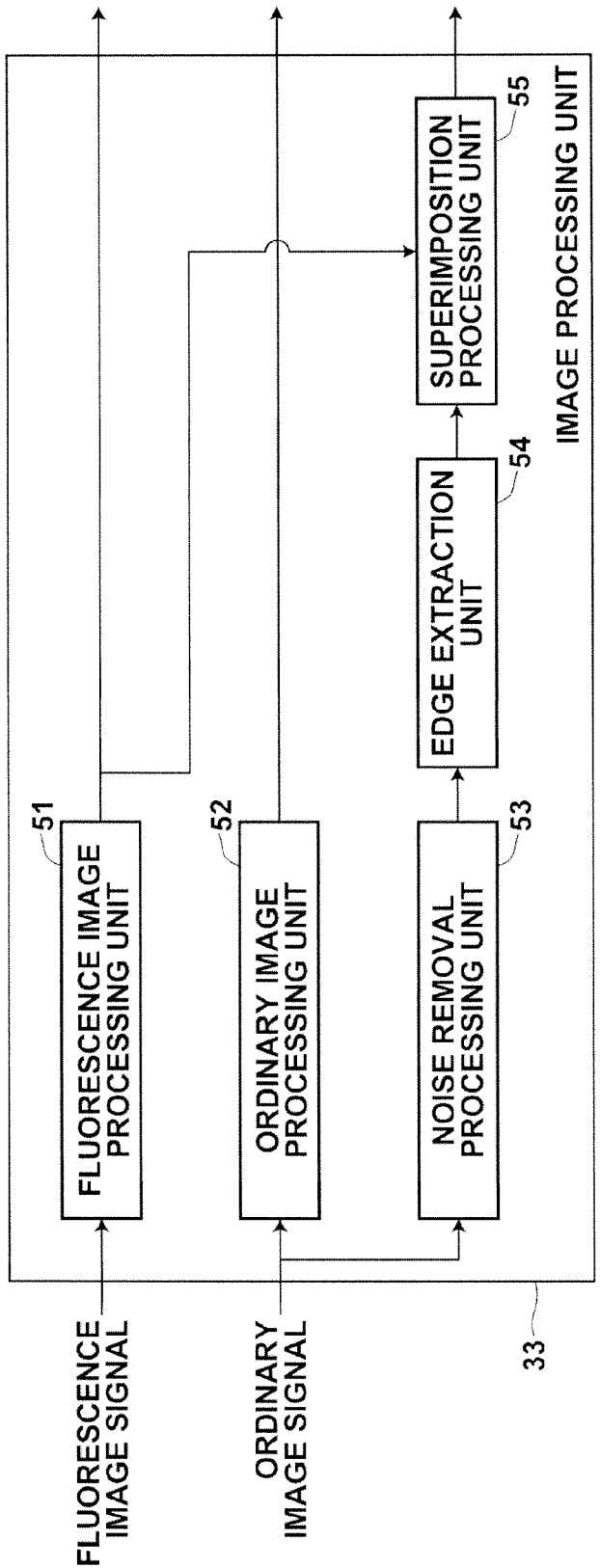
FIG. 5 is a schematic block diagram illustrating the configuration of an image processing unit.

The image processing unit 33 receives ordinary image signals for each frame and fluorescence image signals for each frame that have been read out from the memory 34, and performs predetermined image processing on the image signals, and outputs the processed image signals to a bus. FIG. 5 illustrates more specific configuration of the image processing unit 33.

As illustrated in FIG. 5, the image processing unit 33 includes a fluorescence image processing unit 51, an ordinary image processing unit 52, a noise removal processing unit 53, an edge extraction unit 54 and a superimposition processing unit 55.

The fluorescence image processing unit 51 performs, on the input fluorescence image signals, predetermined image processing that is appropriate for fluorescence images, and outputs the processed fluorescence image signals. In the present embodiment, a fluorescence image of ICG, the outline of which is relatively blurred, is imaged. Therefore, the fluorescence image processing unit 51 performs gradation correction processing and sharpness processing on the fluorescence image signals.

The ordinary image processing unit 52 performs, on the input ordinary image signals, predetermined image processing that is appropriate for ordinary images, and outputs the processed ordinary image signals.

The noise removal processing unit 53 performs noise removal processing on the input ordinary image signals. Specifically, in the present embodiment, the noise removal processing unit 53 performs processing for removing high frequency component noise included in the ordinary image signals. As such processing for removing high frequency component noise, known techniques may be adopted. For example, processing using a median filter may be used.

The edge extraction unit 54 performs edge extraction processing on the ordinary image signals on which noise removal processing has been performed. The edge extraction unit 54 generates outline extraction image signals by extracting outlines of an organ, blood vessels, or the like included in the ordinary image signals by the edge extraction processing. As the edge extraction processing, known techniques may be adopted. For example, processing using a Laplacian filter, processing using a Canny method, or the like may be adopted. In the present embodiment, the aforementioned noise removal processing unit 53 and the edge extraction unit 54 constitute the extraction image generation unit.

The superimposition processing unit 55 generates a superimposition image signal by placing the outline extraction image signal generated by the edge extraction unit 54 on the fluorescence image signal on which image processing has been performed by the fluorescence image processing unit 51.

As illustrated back in FIG. 4, a video output unit 35 receives, through a bus, the ordinary image signals, the fluorescence image signals and the superimposition image signals that have been output from the image processing unit 33, and generates display control signals by performing predetermined processing on the received image signals. The video output unit 35 outputs the display control signals to the monitor 4.

The operation unit 36 receives an input, such as various operation instructions and a control parameter, by an operator or a user. The TG 37 outputs drive pulse signals for driving the high sensitivity imaging device 24 and the imaging device 26 in the imaging unit 20, and an LD driver 45 in the light source apparatus 2, which will be described later. The CPU 38 control the apparatus.

The light source apparatus 2 includes an ordinary light source 40, a condensing lens 42, and a dichroic mirror 43. The ordinary light source 40 outputs ordinary light (white light) L1 in a wide band of wavelengths of approximately 400 to 700 nm. The condensing lens 42 condenses the ordinary light L1 that has been output from the ordinary light source 40. The dichroic mirror 43 passes the ordinary light L1 that has been condensed by the condensing lens 42, and reflects excitation light L2, which will be described later. The dichroic mirror 43 makes the ordinary light L1 and the excitation light L2 enter an entrance end of optical cable LC. As the ordinary light source 40, for example, a xenon lamp is used. Further, a stop (a diaphragm, or an aperture) 41 is provided between the ordinary light source 40 and the condensing lens 42, and the size of the aperture (F-number) is controlled based on a control signal from an ALC (automatic light control) 48.

The light source apparatus 2 includes a near infrared LD light source 44, an LD driver 45, a condensing lens 46, and a mirror 47. The near infrared LD light source 44 outputs, as excitation light L2, near infrared light with wavelengths of 750 to 830 nm. The LD driver 45 drives the near infrared LD light source 44. The condensing lens 46 condenses the excitation light L2 that has been output from the near infrared LD light source 44. The mirror 47 reflects the excitation light L2 condensed by the condensing lens 46 toward the dichroic mirror 43.

The wavelength band of the excitation light L2 is narrower than the wavelength band of ordinary light, which is a wide wavelength band. The excitation light L2 is not limited to light in the aforementioned wavelength band, and is appropriately determined based on the kind of a fluorescent pigment or the kind of autofluorescent living body tissue to be excited.

Next, the action of a rigid endoscope system according to the present embodiment will be described.

The rigid endoscope system of the present embodiment displays a fluorescence image of ICG fluorescence by illumination with excitation light, an ordinary image by illumination with white light, and a superimposition image. The superimposition image is based on the aforementioned superimposition image signals. First, an action of displaying an ordinary image and a fluorescence image will be described.

First, an operator inserts the body cavity insertion unit 30 into a patient's body cavity, and the leading end of the body cavity insertion unit 30 is set in the vicinity of a region to be observed.

Then, ordinary light L1 that has been output from the ordinary light source 40 in the light source apparatus 2 enters the body cavity insertion unit 30 through the condensing lens 42, the dichroic mirror 43 and the optical cable LC. The ordinary light L1 illuminates the region to be observed through the illumination window 30d of the body cavity insertion unit 30. Meanwhile, excitation light L2 that has been output from the near infrared LD light source 44 in the light source apparatus 2 enters the body cavity insertion unit 30 through the condensing lens 46, the mirror 47, the dichroic mirror 43, and the optical cable LC. The excitation light L2 illuminates the region to be observed through the illumination window 30d of the body cavity insertion unit 30 at the same time as illumination of the region to be observed with the ordinary light L1.

Further, an ordinary image based on reflection light that has been reflected from the region to be observed by illumination of the region to be observed with the ordinary light L1 is imaged. Further, a fluorescence image based on fluorescence that has been output from the region to be observed by illumination of the region to be observed with the excitation light L2 is imaged. Here, it is assumed that ICG has been administered to the region to be observed in advance, and fluorescence output from ICG is imaged.

Specifically, when an ordinary image is imaged, ordinary image L3 based on reflection light that has been reflected from the region to be observed by illumination of the region to be observed with ordinary light L1 enters the insertion member 30b from leading end 30Y of the insertion member 30b. The ordinary image L3 is guided by a lens group in the insertion member 30b, and output toward the imaging unit 20.

The ordinary image L3 that has entered the imaging unit 20 is reflected by the dichroic prism 21 at a right angle toward the imaging device 26. Further, an image of the ordinary image L3 is formed on the imaging plane of the imaging device 26 by the second image formation optical system 25. The imaging device 26 sequentially images the ordinary image L3 at a predetermined frame rate.

Ordinary image signals are sequentially output from the imaging device 26, and CDS/AGC (correlated double sampling/automatic gain control) processing and A/D conversion processing are performed on the ordinary image signals in the imaging control unit 27. The processed ordinary image signals are sequentially output to the processor 3 through the cable 5.

The ordinary image signals that have entered the processor 3 are stored in the memory 34 after temporarily being stored in the ordinary image input controller 31. The ordinary image signals for each frame are read out from the memory 34, and predetermined image processing is performed on the ordinary image signals by the ordinary image processing unit 52 in the image processing unit 33. The processed ordinary image signals are sequentially output to the video output unit 35.

The video output unit 35 generates display control signals by performing predetermined processing on the ordinary image signals that have entered the video output unit 35. Further, the video output unit 35 sequentially outputs the display control signals for each frame to the monitor 4. The monitor 4 displays an ordinary image based on the input display control signals.

Meanwhile, when a fluorescence image is imaged, fluorescence image L4 based on fluorescence that has been output from the region to be observed by illumination of the region to be observed with excitation light enters the insertion member 30b from leading end 30Y of the insertion member 30b. The fluorescence image L4 is guided by a lens group in the insertion member 30b, and output toward the imaging unit 20.

The fluorescence image L4 that has entered the imaging unit 20 passes through the dichroic prism 21 and the excitation light cut filter 22. Further, an image of the fluorescence image L4 is formed on the imaging plane of the high sensitivity imaging device 24 by the first image formation optical system 23. The high sensitivity imaging device 24 images the fluorescence image L4 at a predetermined frame rate.

Fluorescence image signals are sequentially output from the high sensitivity imaging device 24, and CDS/AGC (correlated double sampling/automatic gain control) processing and A/D conversion processing are performed on the fluorescence image signals in the imaging control unit 27. The processed fluorescence image signals are sequentially output to the processor 3 through the cable 5.

The fluorescence image signals that have entered the processor 3 are stored in the memory 34 after temporarily being stored in the fluorescence image input controller 32. The fluorescence image signals for each frame are read out from the memory 34, and predetermined image processing is performed on the fluorescence image signals by the fluorescence image processing unit 51 in the image processing unit 33. The processed fluorescence image signals are sequentially output to the video output unit 35.

The video output unit 35 generates display control signals by performing predetermined processing on the fluorescence image signals that have entered the video output unit 35. Further, the video output unit 35 sequentially outputs the display control signals for each frame to the monitor 4. The monitor 4 displays a fluorescence image based on the input display control signals.

FIG. 6 is a diagram illustrating an example of an ordinary image and a fluorescence image displayed on the monitor 4 by the aforementioned action. In FIG. 6, the ordinary image is represented by a line drawing. However, an actual ordinary image is a color image.

When the ordinary image and the fluorescence image are displayed, as illustrated in FIG. 6, in some cases, an observer (user) wants to know where the light output portion of the fluorescence image is located in the ordinary image (in other words, the location or an approximate position of a light output portion of the fluorescence image in the ordinary image). In such a case, the observer inputs an instruction for displaying a superimposition image by using the operation unit 36. The superimposition image is displayed based on the instruction. Next, the action of displaying the superimposition image will be described.

Specifically, when a synthesis image is displayed, ordinary image signals that have been input to the image processing unit 33 are input to the noise removal processing unit 53. After the noise removal processing unit 53 performs noise removal processing on the ordinary image signals, the processed ordinary image signals are input to the edge extraction unit 54. Further, the edge extraction unit 54 performs edge extraction processing on the ordinary image signals on which noise removal processing has been performed. Accordingly, outline extraction image signals are generated.

The outline extraction image signals that have been generated based on the ordinary image signals, as described above, and fluorescence image signals that have been output from the fluorescence image processing unit 51 are input to the superimposition processing unit 55. The superimposition processing unit 55 generates superimposition image signals by superimposing the input outline extraction image signals on the input fluorescence image signals.

The superimposition image signals that have been generated by the superimposition processing unit 55 are input to the video output unit 35. The video output unit 35 generates display control signals by performing predetermined processing on the input superimposition image signals. Further, the video output unit 35 sequentially outputs the display control signals for each frame to the monitor 4. The monitor 4 displays a superimposition image based on the input display control signals. FIG. 7 is a diagram illustrating an example of a superimposition image displayed on the monitor 4 by the aforementioned action. In FIG. 7, an outline extraction image displayed based on outline extraction image signals is displayed in white. However, the actual color of the outline extraction image is not limited to white. The actual outline extraction image may be displayed in a different color other than black.

In the superimposition image, the outline extraction image generated based on the ordinary image is superimposed and displayed on the fluorescence image. Therefore, it is possible to immediately recognize where a light output portion of the fluorescence image is located in the ordinary image.

When the superimposition image is displayed as described above, an ordinary image that is displayed at the same time may be displayed in such a manner that an outline or outlines of the ordinary image are enhanced. Specifically, an outline enhancement processing unit may be further provided to display the ordinary image the outline or outlines of which are enhanced by performing outline enhancement processing on ordinary image signals. The outline enhancement processing unit performs outline enhancement processing, such as edge enhancement processing, on ordinary image signals. Consequently, it is possible to immediately recognize correspondence between the ordinary image and the outline extraction image that has been superimposed on the fluorescence image.

Further, in the rigid endoscope system of the aforementioned embodiment, all outlines included in the ordinary image are extracted, and the extracted outlines are superimposed on the fluorescence image. However, it is not necessary that all the outlines are extracted. For example, an outline or outlines of only some region or regions, such as an organ, in the ordinary image may be extracted to obtain an outline extraction image, and the outline extraction image may be superimposed on the fluorescence image. Specifically, only an outline or outlines of a closed region or regions that are larger than or equal to a predetermined size may be extracted from all the outlines in the ordinary image to generate an outline extraction image. Further, the outline extraction image may be superimposed on the fluorescence image. When such an outline extraction image is superimposed on the fluorescence image, it is possible to delete or exclude unneeded outlines, such as an outline composed of a short segment and an outline forming a small closed region. Therefore, it is possible to more clearly observe the light output portion of the fluorescence image as well as recognizing the location of the light output portion of the fluorescence image. The closed region is formed by using not only an outline or outlines of an organ, blood vessels, or the like in the ordinary image but also the outline of the whole ordinary image (circles illustrated in FIGS. 6 and 7) The outline or outlines in the ordinary image that correspond to the outline extraction image may be displayed in such a manner that the outline or outlines are enhanced also in this case. Further, different display modes, such as a display mode of superimposing an outline extraction image of all outlines on a fluorescence image, as described above, a display mode of superimposing an outline extraction image of a part of outlines, such as an outline of an organ, on a fluorescence image, and a display mode of displaying a fluorescence image without an outline extraction image superimposed on the fluorescence image, may be provided in such a manner that at least two of the different modes are switchable.

When a fluorescence image of ICG is observed as in the rigid endoscope system of the aforementioned, the area of a light output portion is small during a short time period after administration of ICG to a region to be observed. However, when a certain time period passes after administration of ICG, the area of the light output portion of ICG becomes larger. Therefore, recognition of the location of the light output portion becomes relatively easy, and superimposition of the outline extraction image on the fluorescence image, as described above, is not necessary in some cases.

Therefore, in the rigid endoscope system of the aforementioned embodiment, the area of a light output portion in the fluorescence image may be calculated, and when the area becomes larger than or equal to a predetermined threshold value, the fluorescence image may displayed without displaying the outline extraction image. Consequently, it is possible to more clearly observe the light output portion of the fluorescence image. As a method for not displaying the outline extraction image, a method in which the outline extraction image is not generated may be adopted. Specifically, none of noise removal processing, edge extraction processing and superimposition processing is performed. Alternatively, a method in which the outline extraction image is generated but not displayed may be adopted.

In the aforementioned embodiment, the ordinary image and the fluorescence image are imaged at the same time by illuminating a region to be observed with ordinary light and excitation light at the same time. However, it is not necessary that the image display apparatus of the present invention is configured in such a manner. For example, the region to be observed may be illuminated alternately with ordinary light and with excitation light by time division, and the ordinary image and the fluorescence image may be imaged by time division.

In the aforementioned embodiment, the fluorescence image is imaged by the first imaging system. However, it is not necessary that the fluorescence image is imaged. Alternatively, an image based on the light absorption characteristics of the region to be observed by illumination of the region to be observed with special light may be imaged.

In the aforementioned embodiment, the image display apparatus of the present invention is applied to a rigid endoscope system. However, application of the image display apparatus of the present invention is not limited to the rigid endoscope system. For example, the image display apparatus of the present invention may be applied to a different kind of endoscope system including a soft endoscope apparatus. Further, it is not necessary that the image display apparatus of the present invention is applied to endoscope systems. The image display apparatus of the present invention may be applied to a so-called video-type medical image imaging apparatus that does not include an insertion unit, which is inserted into a patient's body cavity.

What is claimed is:

1. An image display apparatus comprising:
    an image obtainment unit that obtains a visible image based on light output from a region to be observed by illumination of the region to be observed with visible light, and a special image based on light output from the region to be observed by illumination of the region to be observed with special light in a wavelength band that is different from the wavelength band of the visible light;
    an extraction image generation unit that generates an extraction image by extracting at least one outline included in the visible image;
    a superimposition processing unit that generates a superimposition image by superimposing the extraction image generated by the extraction image generation unit on the special image; and
    a display unit that displays the superimposition image generated by the superimposition processing unit.

2. An image display apparatus, as defined in claim 1, wherein the extraction image generation unit generates the extraction image by extracting at least one closed region having a predetermined size or larger included in the visible image.

3. An image display apparatus, as defined in claim 1, wherein the display unit does not display the superimposition image, but displays the special image on which the extraction image is not superimposed when the size of a portion of the special image that represents a region outputting light by illumination with the special light is greater than or equal to a predetermined threshold value.

4. An image display apparatus, as defined in claim 1, the apparatus further comprising:
    an outline enhancement processing unit that performs outline enhancement processing on the visible image,
    wherein the display unit displays the visible image on which the outline enhancement processing has been performed.

5. An image display apparatus, as defined in claim 1, wherein the special light comprises excitation light.

6. An image display apparatus, as defined in claim 5, wherein the excitation light comprises near infrared light.

7. An image display apparatus, as defined in claim 1, wherein the visible light comprises white light.

8. An image display method comprising:
    obtaining a visible image based on light output from a region to be observed by illumination of the region to be observed with visible light, and a special image based on light output from the region to be observed by illumination of the region to be observed with special light in a wavelength band that is different from the wavelength band of the visible light;
    generating an extraction image by extracting at least one outline included in the visible image;
    generating a superimposition image by superimposing the generated extraction image on the special image; and
    displaying the generated superimposition image.

9. An image display apparatus, as defined in claim 1, wherein the extraction image generation unit extracts all outlines included in the visible image.

10. An image display apparatus, as defined in claim 1, wherein the extraction image generation unit extracts all outlines included in the visible image, and
    wherein the display unit comprises a plurality of display modes, a first display mode of superimposing an outline extraction image of all outlines on the special image and a second display mode of superimposing an outline extraction image of said at least one outline included in the visible image on the special image.

11. An image display apparatus, as defined in claim 10, wherein the plurality of display modes are switchable.

12. An image display apparatus, as defined in claim 8, wherein the generating the extraction image further extracts all outlines included in the visible image.

13. An image display apparatus, as defined in claim 12, wherein the generating the extraction image further extracts all outlines included in the visible image, and
    wherein the displaying further displays the generated superimposition image according to a plurality of display modes, a first display mode of superimposing an outline extraction image of all outlines on the special image and a second display mode of superimposing an outline extraction image of said at least one outline included in the visible image on the special image.

14. An image display apparatus, as defined in claim 13, wherein the plurality of display modes are switchable.

* * * * *